(12) United States Patent
Leahy et al.

(10) Patent No.: US 7,606,821 B2
(45) Date of Patent: Oct. 20, 2009

(54) METHOD AND SYSTEM FOR PREVENTING FRAUDULENT ACTIVITIES

(75) Inventors: Scott Leahy, San Jose, CA (US); Jeffrey Taylor, Los Altos, CA (US); Chris Lalonde, Campbell, CA (US); Ajay Agrawal, Cupertino, CA (US); Kevin H Embree, Austin, TX (US); Jeffrey L. King, Campbell, CA (US); Andy Brown, Mt. View, CA (US); Mathew Gene Henley, Campbell, CA (US)

(73) Assignee: eBay Inc., San Jose, CA (US)

( * ) Notice: Subject to any disclaimer, the term of this patent is extended or adjusted under 35 U.S.C. 154(b) by 431 days.

(21) Appl. No.: 10/883,454

(22) Filed: Jun. 30, 2004

(65) Prior Publication Data

US 2006/0021031 A1    Jan. 26, 2006

(51) Int. Cl.
  *G06F 17/30* (2006.01)
(52) U.S. Cl. ............................. 707/102; 726/26; 726/27
(58) Field of Classification Search .................... 707/3, 707/4, 9, 10, 102; 709/206; 726/22, 26–27
  See application file for complete search history.

(56) References Cited

U.S. PATENT DOCUMENTS

| | | | |
|---|---|---|---|
| 5,706,507 A * | 1/1998 | Schloss | 707/10 |
| 5,835,712 A * | 11/1998 | DuFresne | 707/10 |
| 6,092,194 A * | 7/2000 | Touboul | 726/24 |
| 6,286,001 B1 * | 9/2001 | Walker et al. | 707/9 |
| 6,510,458 B1 * | 1/2003 | Berstis et al. | 707/10 |
| 6,604,131 B1 * | 8/2003 | Warris et al. | 709/205 |
| 6,874,084 B1 * | 3/2005 | Dobner et al. | 713/156 |
| 7,068,190 B2 * | 6/2006 | Satomi et al. | 341/22 |
| 2002/0016910 A1 * | 2/2002 | Wright et al. | 705/51 |
| 2003/0097593 A1 * | 5/2003 | Sawa et al. | 713/201 |
| 2003/0163714 A1 * | 8/2003 | Nortung | 713/189 |
| 2004/0078422 A1 * | 4/2004 | Toomey | 709/202 |
| 2004/0123157 A1 * | 6/2004 | Alagna et al. | 713/201 |
| 2006/0089978 A1 * | 4/2006 | Lee et al. | 709/219 |

\* cited by examiner

*Primary Examiner*—Vincent Boccio
(74) *Attorney, Agent, or Firm*—Schwegman, Lundberg, Woessner, P.A.

(57) ABSTRACT

A method and system to protect users against potentially fraudulent activities associated with spoof web sites are described. According to one aspect of the present invention, the URL of a document downloaded via a web browser client is compared to the URLs in a list of URLs for known spoof sites. If the URL for the downloaded document is found in the list of URLs for known spoof sites, a security indicator is displayed to the user to indicate to the user that the downloaded document is associated with a known spoof site. According to another aspect of the invention, a security server maintains a master black list and periodically communicates updates of the master black list to the local list of a client security application.

12 Claims, 18 Drawing Sheets

METHOD AND SYSTEM FOR PREVENTING FRAUDULENT ACTIVITIES

FIELD OF THE INVENTION

The present invention relates generally to Internet security, and in particular, to a method and system for protecting users against potentially fraudulent activities associated with spoof web sites.

BACKGROUND OF THE INVENTION

The advance of computer and networking technologies has resulted in a significant increase in the number of people who conduct business and execute financial transactions online. For example, people are using personal computers connected to the Internet to perform online banking, purchase goods and services, and to conduct business generally. Many of the activities that people perform online include accessing or exchanging data that is of a confidential and private nature. Accordingly, to ensure the data remains confidential and private, enterprises that offer online services require systems and tools to protect their customer's data.

One of the most common schemes for protecting confidential and private data is the ubiquitous username and password scheme. For example, many enterprises require their customers to set up accounts by first establishing a unique username and password. Each time the customer would like to gain access to his private and confidential data, the customer is requested to verify his identity by entering his username and password. Consequently, to protect confidential and private data, the customer must take great care to protect his username and password from being discovered by others. If a user allows his username and password to fall into the wrong hands, often times other private data, such as credit card numbers and/or social security numbers, are easily compromised as well.

Unfortunately, the general increase in online activities has also seen an increase in the number of unscrupulous persons seeking to commit fraudulent activates online, particularly online identity theft. Naturally, the perpetrators of these crimes tend to target the most vulnerable, in this case, those with little experience and familiarity with the Internet and online enterprises.

One of the most common identity theft schemes involves the use of "spoof" web sites. A spoof web site is a web site that has purposefully been designed to imitate the web site of a more popular and legitimate enterprise. A perpetrator will often lead people to the spoof web site by mass mailing spoof emails. These deceptive emails will request that the recipient of the email respond by navigating to a spoof web site and provide personal information, such as his or her username and password. Once the perpetrators have the unsuspecting person's username and password, the perpetrators can use the username and password to gain access to that person's account at the legitimate web site that the spoof site is setup to imitate. Consequently, this type of scheme often targets financial web sites and large online retailers.

SUMMARY OF THE INVENTION

A method and system for protecting users against potentially fraudulent activities are provided. According to one embodiment of the invention, a client application includes a comparator module to compare the URL of a downloaded document to the URLs in a black list—a list of URLs for documents associated with known spoof sites. In addition, the client application includes a display indicator module to display a security warning if the URL of the downloaded document matches a URL from the list of URLs for documents associated with known spoof sites. For one embodiment of the invention, the client application's list of URLs for documents associated with known spoof sites is periodically updated via a network connected security server.

According to another embodiment of the invention, a client application includes a comparator module to compare the URL of a downloaded document to the URLs in a white list—a list of URLs for documents associated with known trusted sites. In addition, the client application includes a display indicator module to display a security indicator to indicate that the downloaded document is associated with a trusted site if the URL of the downloaded document matches a URL from the list of URLs for documents associated with known trusted sites. For one embodiment of the invention, the client application's list of URLs for documents associated with known trusted sites is periodically updated via a network connected security server.

According to another embodiment of the invention, a client application includes a comparator module to compare the URL of a downloaded document to the IP address in a white list—a list of IP addresses for documents served from known trusted sites. In addition, the client application includes a display indicator module to display a security indicator to indicate that the downloaded document is associated with a trusted site if the IP address of the downloaded document matches the list of IP addresses for documents associated with known trusted sites. For one embodiment of the invention, the client application's list of URLs for documents associated with known trusted sites is periodically updated via a network connected security server.

According to yet another embodiment of the invention, the client application includes a password detection module. The password protection module detects when a user is attempting to submit a password associated with an account at a particular web site to a server that is not associated with that particular web site.

Other aspects of the present invention will be apparent from the accompanying figures and from the detailed description that follows.

BRIEF DESCRIPTION OF THE DRAWINGS

The present invention is illustrated by way of example and not limitation in the figures of the accompanying drawings, in which like references indicate similar elements and in which.

DETAILED DESCRIPTION

A method and system for protecting users against fraudulent activities are described. In the following description, for purposes of explanation, numerous specific details are set forth in order to provide a thorough understanding of the present invention. It will be evident, however, to one skilled in the art that the present invention may be practiced without these specific details.

One advantage of the present invention is that it provides a simple and effective way for novice and advanced Internet users to detect, and thereby avoid interaction with, spoof web sites. For one embodiment of the present invention, a client toolbar application executes on a user's PC in conjunction with a web browser application. The client toolbar application includes a universal resource locator, or URL, comparator module to compare the URL of a recently downloaded document to the URLs in a list of URLs associated with known spoof sites. If the comparator module determines that the URL of the recently downloaded document matches a URL listing in the list of URLs associated with known spoof sites, a visual display indicator module displays a security warning on the toolbar to warn the user that he or she is viewing a spoof site.

In another embodiment of the present invention, a client toolbar application executes on a user's PC in conjunction with a web browser application. The client toolbar application includes a comparator module to compare the URL of a downloaded document with the URLs in a list of URLs associated with known trusted sites. If the comparator module determines that the URL of the downloaded document matches a URL in the list of trusted sites, a visual display indicator indicates to the user that the downloaded document is associated with a trusted site.

An embodiment of the present invention is also advantageous for its ability to detect when a user is submitting a password associated with a particular account, to a server not associated with that account. For example, one embodiment of the invention includes a password detection module that detects when a password is being submitted to a server. If the password is known to be associated with a particular account, and the server to which the password is being submitted is not associated with that particular account, then the password detection module warns the user that he is submitting a password associated with a particular account to a server not associated with the account.

Figure 1:
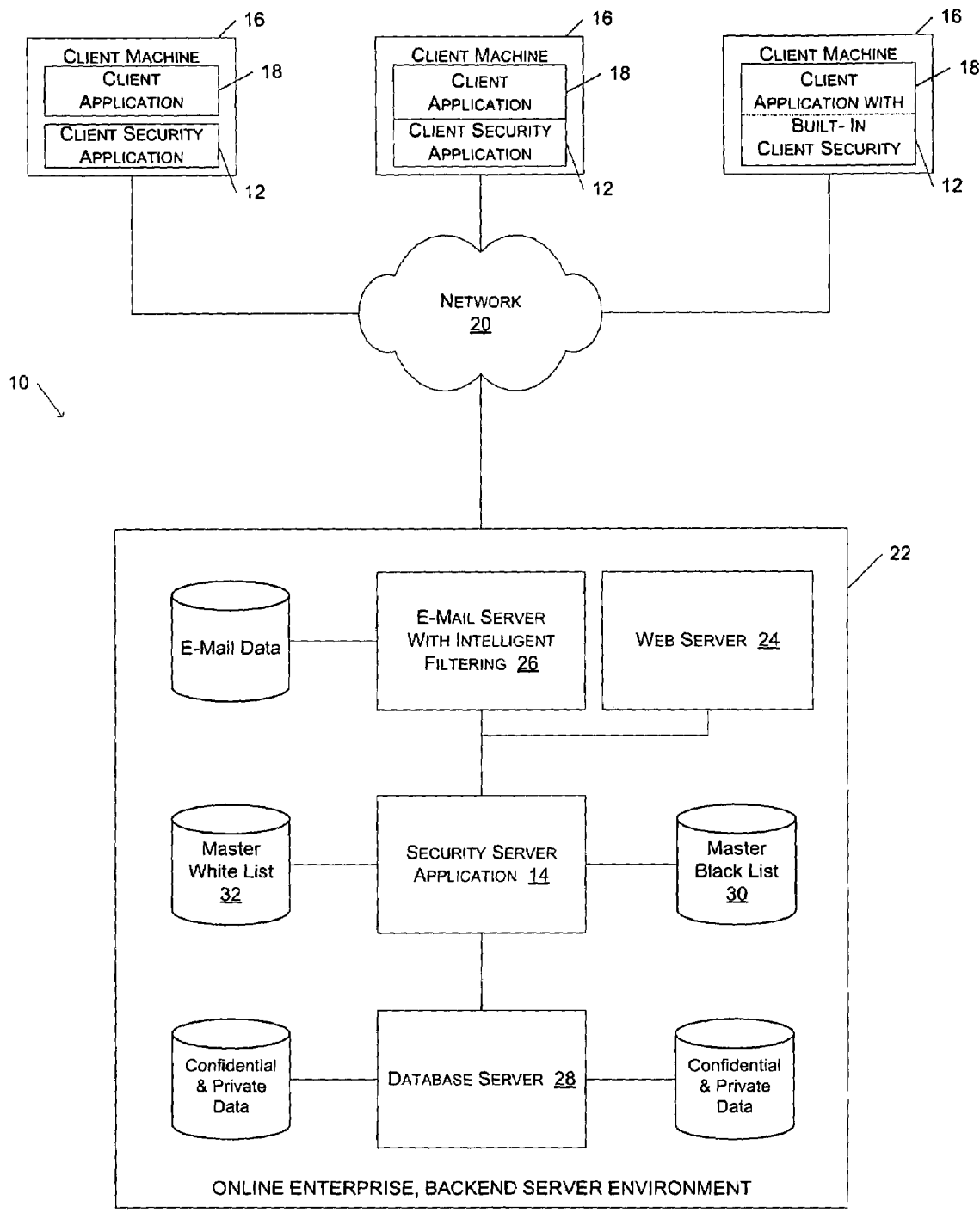
FIG. 1 illustrates an embodiment of the present invention including a client security application and a security server application, implemented in a client-server network environment.

FIG. 1 illustrates a client-server network environment 10 including a client security application 12 and a security server application 14, consistent with an embodiment of the present invention. The client-server network environment 10 illustrated in FIG. 1 includes three client machines 16 connected via a network 20 to various servers in a backend server environment 22. Each client machine 16 is capable of executing a client application 18 that facilitates the browsing of documents hosted and served by the web server 24 of the backend server environment 22. For one embodiment of the present invention, the client security application 12 operates in conjunction with a client application 18 to help users identify spoof sites and trusted sites while browsing documents via the network 20. For example, the client application 18 may be a web browser application, such as Microsoft Internet Explorer®. By entering a universal resource locator (URL) into the address bar of the web browser, a user is able to download and view documents that are served by the web server 24. For each document the user downloads via the web browser 18, the client security application 12 displays a security indicator to indicate a security ranking for the document. For purposes of the present invention, the term "document" is used to describe any file produced by an application, such as an audio file, an email, a video file, or a web page.

In addition to the web server 24, the backend server environment 22 includes an e-mail server 26, a database server 28, and a security server application 14. The database server 28 controls and maintains user account data that is accessible to users via documents served by web server 24. As described in greater detail below, the security server application 14 operates in conjunction with the client security application 12 to ensure that the client security application has a current list of spoof sites and trusted sites.

As illustrated in FIG. 1, the client security application 12 may be a stand-alone application, or it may be dynamically linked to the client application 18. Alternatively, the client security application 12 may be a tightly integrated subcomponent of the client application 18. For one embodiment of the invention, the client security application 12 appears as a toolbar that is attachable to a window of a web browser application 18. In an alternative embodiment of the invention, the user interface of the client security application 12 may vary. For example, the client security application 12 may appear in the system tray of a windowing operating system, or as one or more pop-up windows. Alternatively, the client security application may run in the background, completely behind the scenes with no UI, and only display a warning when a potential spoof site is detected.

For one embodiment of the present invention, the security server application 14 includes what is referred to as a master "black list" 30—a list of universal URLs for documents that are associated with known spoof sites. For example, the black list 30 includes a listing of URLs that someone has verified as being associated with a known spoof site or spoof document. A spoof site is a web site that is set up to imitate the web site of another well-known and reputable online enterprise. An unscrupulous fraudster often achieves this by selecting a domain name that slightly differs from the domain name of the well-known site. For example, a spoof site for the well-known online retailer Amazon.com, with the URL www.amazon.com, may use the domain name amazin.com, and the URL www.amazin.com. If a user unwittingly enters "www.amazin.com" in the address bar of his or her web browser, a spoof site will appear that imitates the more popular and legitimate retail site of Amazon.com.

In addition to a black list, the security server application 14 may include what is referred to as a master "white list" 32—a list of URLs for documents that are associated with known trusted sites. Using a local white list, the client security application 12 can identify known trusted sites. Accordingly, the client security application 12 can display a security indicator to indicate that the document being viewed is associated with a known trusted site.

The present invention provides for a system and method to facilitate identifying, and thereby avoiding interaction with, known spoof sites. For example, for one embodiment of the invention, once a web site or document has been identified as a spoof site, the URL of the site or document is added to the master black list 30 of the security server application 14. The client security application maintains a local black list, which may be automatically updated by the master black list 30 of the security server application 14 on a periodic basis. When a user enters a URL in the address bar of his or her web browser 18, the client security application 12 will compare the user-entered URL to the URLs in the local black list, for example, the local list of known spoof sites. If the URL input by the user matches a URL in the local black list, the client security application 12 displays a security warning in the toolbar of the web browser window to notify the user that the URL is associated with a known spoof site. Consequently, if a user unintentionally enters the URL, www.amazin.com, instead of www.amazon.com the user will be notified that the site is a spoof, and therefore the user can avoid unintentionally submitting confidential and private information, such as his username and password for his account held at Amazon.com.

In an alternative embodiment, rather than maintain a local copy of the black list and white list at the client security application 12, the client security application 12 communicates the URL of the document being viewed to the security server application 14. The security server application 14 then compares the URL to the master black list 30 or master white list 32, and reports the appropriate security ranking to the client security application 12. Accordingly, the client security application 12 will display a security indicator to the user based on the comparison performed by the security server application 14.

The present invention also provides a user with the ability to report potential spoof sites via email. For example, for one embodiment of the invention, the client security application 12, via a toolbar user interface, presents the user with the option to send an email to the email server 26 to report a suspicious site. The email may be automatically generated to report the URL of the document that is being viewed, or alternatively, the user may be prompted to enter the URL of the suspicious site. When the email is received at the email server 26, it is automatically processed according to its contents. For example, the email server 26 has intelligent filtering capabilities to automatically react to receiving an email. For example, the email server 26 may automatically react by routing the email to the proper administrative person for review, or alternatively, the email server 26 may automatically extract the URL and add it to a list of suspicious URLs to be verified. In addition, the email server 26 may automatically generate a response email indicating to the user what further action to take.

Figure 2:
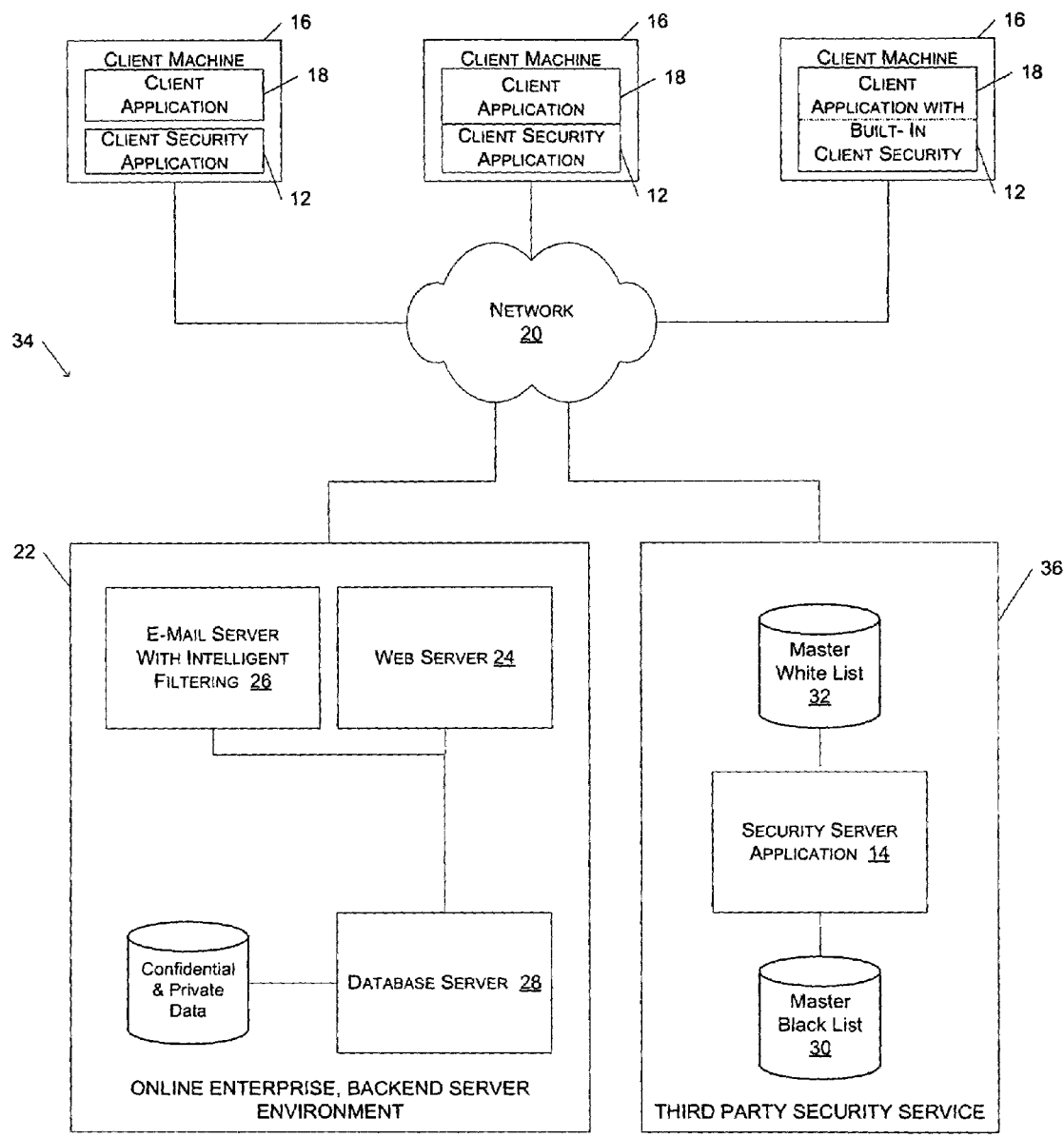
FIG. 2 illustrates another embodiment of the present invention including a client security application and a security server application hosted by a third party, implemented in a client-server environment.

FIG. 2 illustrates an alternative embodiment of the invention as implemented in a client-server environment 34, including a client security application 12 and a security server application 14 hosted by a third party. The system illustrated in FIG. 2 is similar to that of FIG. 1, however, the security server application 14 is hosted by a third party 36 remote from the backend server environment 22 of the online enterprise. With this particular embodiment of the invention, the security server application 14 may serve as a central clearinghouse for several online enterprises. For example, the security server application 14 may maintain a list of spoof sites that imitate various online sites, including the site hosted by the web server 24 illustrated in FIG. 2.

Figure 3:
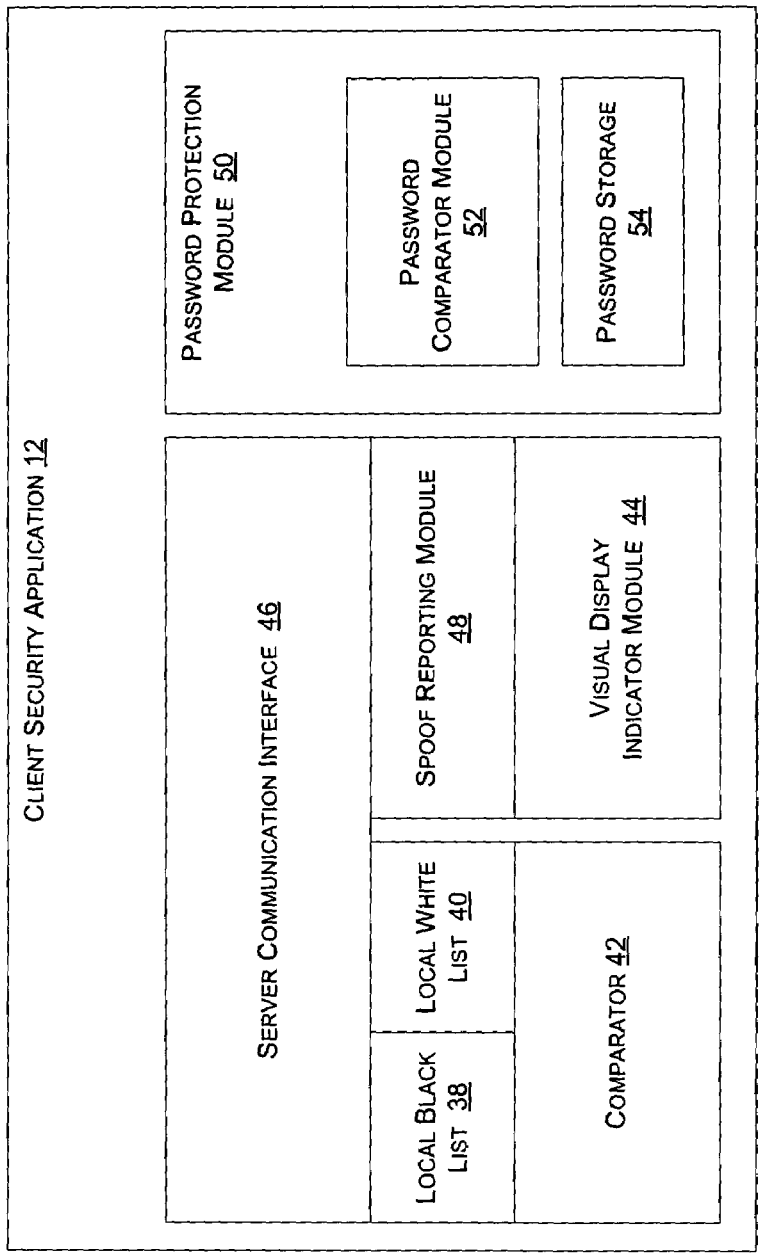
FIG. 3 illustrates a client security application for an embodiment of the present invention.

FIG. 3 illustrates a block diagram of a client security application 12 for one embodiment of the present invention. The client security application 12 illustrated in FIG. 3 includes a local black list 38 and a local white list 40, a comparator 42 and a visual display indicator module 44. For one embodiment of the invention, the comparator module 42 compares the URL of a document recently downloaded via a web browser client 18 with the URLs in the local black list 38 and the local white list 40. If the URL of the recently download document matches a URL in the local black list 38 (e.g., the local list of known spoof sites), the visual display indicator module 44 will cause a security warning to be displayed to the user. Similarly, if the URL of the recently downloaded document matches a URL in the local white list 40 (e.g., the local list of known trusted sites), the visual display indicator module 44 will cause a security indicator to be displayed, indicating that the downloaded document is associated with a known trusted site.

In an alternative embodiment, the comparator 42 may be an internet protocol (IP) address comparator, and the local black 38 and white lists 40 may list IP addresses instead of URLs. Accordingly, the IP address comparator 42 may compare the IP address of the server from which a document was downloaded to the IP addresses listed in the local black list 38 and white list 40. If a match is found, the visual display indicator module 44 displays the appropriate message, depending on which list contained the matching address.

The client security application 12 illustrated in FIG. 3 also includes a server communication interface 46 and a spoof-reporting module 48. For one embodiment of the invention, the server communication interface 46 serves as the client security application's 12 interface to a security server, such as the security server 14 illustrated in FIG. 1. Via the security server interface 46, the client security application 12 receives updates to the local black list 38 and white list 40 on a periodic basis. For example, the security server application 14 may send the client security application 12 updates from its master black list 30 or master white list 32 on a daily, or nightly, basis. Alternatively, the security server application 14 may send the client security application 12 updates from its master black list 30 and white list 32 every time a new entry is made into one of the master lists.

In addition, the spoof-reporting module 48 of the client security application 12 provides the user with the ability to communicate potential spoof sites to the security server application 14. For one embodiment, the user interface of the client security application 12 presents the user with the option to report suspicious web sites. When the user selects the option to report a suspicious site, the spoof-reporting module 48 automatically generates an email that may be transmitted via the server communication interface 46 over a network 20 to an email server 26. Accordingly, the email server 26 may route the email containing the potential spoof URL to the proper administrative person for review.

The client security application 12 may also include a password protection module 50. For one embodiment of the invention, the password protection module 50 detects when a user is attempting to submit a password associated with a particular account to a server that is not associated with that particular account. For example, assume a user has selected the password, "smith-007" for an account held at Amazon.com. If the user enters "smith-007" into the password text field of a form, and then attempts to submit (e.g., by posting) the form to a site other than Amazon.com, the password protection module will temporarily halt the submission and notify the user that he is submitting his Amazon.com password to a site that is not associated with Amazon.com.

The password protection module 50 includes a password comparator module 52 and a password storage module 54. The password storage module 54 stores a user's password for a particular site, along with the URLs associated with the particular site. For one embodiment of the invention, the password protection module 50 detects when a user is submitting a password by scanning a form that has been posted to a particular URL. For example, the password protection module 50 may scan the form for text fields labeled as password fields. Once the password protection module detects that a user is attempting to submit a password via a form, the password comparator module 52 compares the password being submitted with one or more passwords in the password storage module 54. If the password being submitted matches a password in the password storage 54, the password comparator checks the URL of the server to which the password is being submitted, or posted. If the URL to which the server is being submitted does not match the URL associated with the password in the password storage 54, the client security application 12 temporarily halts the posting of the form and warns the user that he or she is attempting to submit a password for an account associated with a particular URL, to a site that is not associated with that particular URL.

Figure 4:
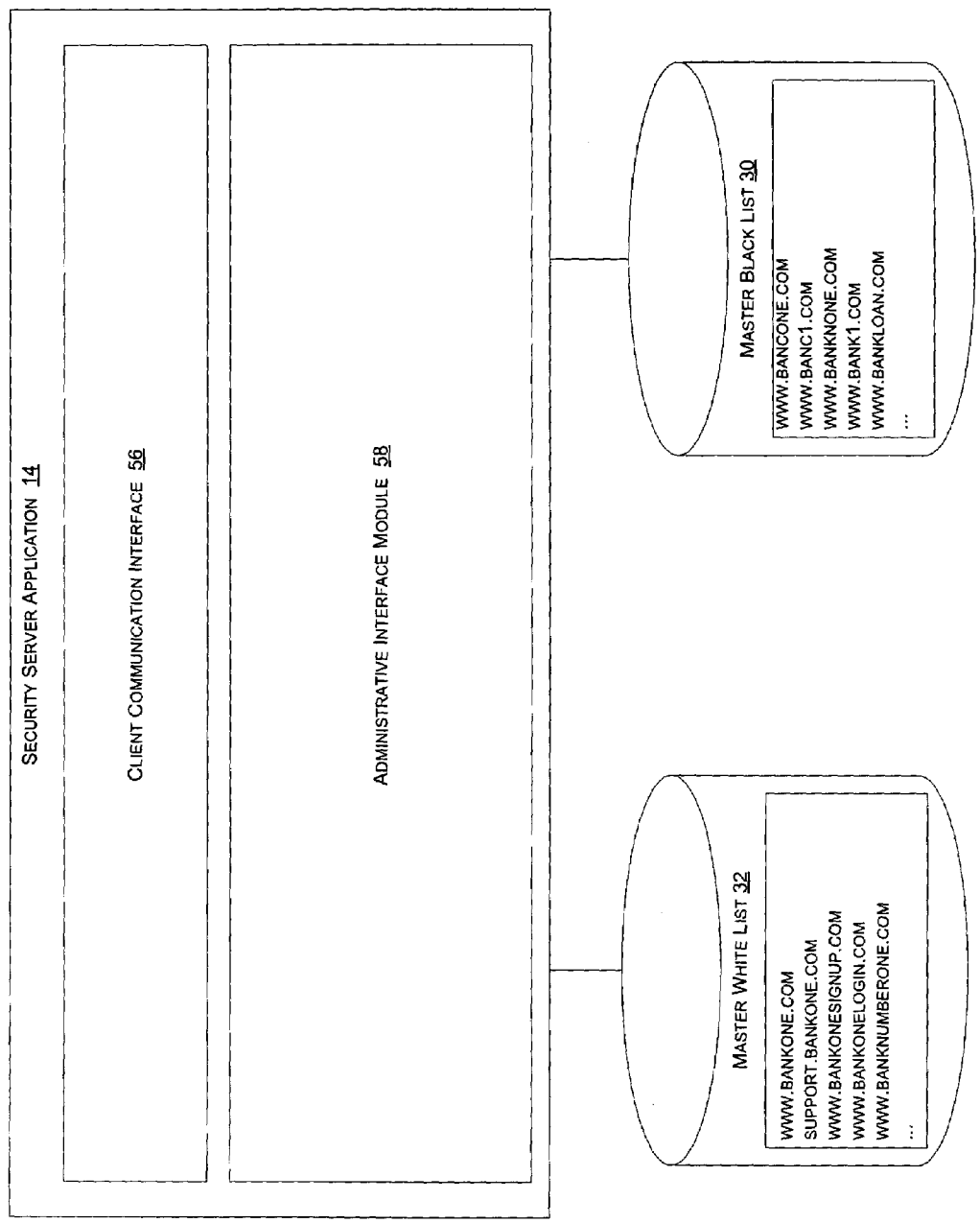
FIG. 4 illustrates a client security application for another embodiment of the present invention.

FIG. 4 illustrates a security server application 14 consistent with one embodiment of the present invention. As illustrated in FIG. 4, the security server application 14 includes a client communication interface 56, an administrative interface module 58, a master black list 30, and a master white list 32. The security server application 14 may be hosted and administered by a single online enterprise, in which case the server 14 may be integrated into the enterprise's backend server environment 22. In such a configuration, the master white list 32 of the security server may be populated only with the domain names assigned to that particular enterprise. Consequently, only documents hosted within those domains will have URLs that are considered to be from a trusted site. Or alternatively, a third party may host the security server application 14. When hosted by a third party, the master white list 32 may be configured to include URLs or domain names of several online enterprises. Although the master white list 32 illustrate in FIG. 4 is shown to include URLs, it will be appreciated that the master white list 32 may contain IP addresses of servers associated with a particular online enterprise.

The client communication interface 56 serves as the interface to the client security application 12. Via the client communication interface 56, the security server application 14 communicates updated master list information from the master lists 30 and 32 to the local lists 38 and 40 of each client security application 12. For example, the security server application 14 may be configured to send list updates to the client security applications 12 on a periodic basis, for instance, as necessary to keep the clients' local lists up to date.

The client communication interface 56 of the security server application 14 may also receive potential spoof sites from the spoof-reporting module 48 of the client security application 12. For example, if a user believes that he has downloaded a document associated with a spoof site, the user may use the spoof-reporting module 48 of the client security application 12 to report the potential spoof site to an administrator of the security server application 14. For one embodiment of the invention, reporting of spoof sites is done via email.

For one embodiment of the invention, an administrator uses the administrative interface module 58 to review URLs that have been submitted by users as potential spoof sites. In addition, the administrative interface module may be used to maintain the master black list 30 and master white list 32. For example, via the administrative interface module 58, an administrator may add or delete entries to each master list 30 and 32 as new spoof sites and trusted sites are identified and verified. For one embodiment of the invention, the administrative interface includes a feature that allows the administrator to forward potential spoof site emails to other online enterprises for verification.

Figure 5:
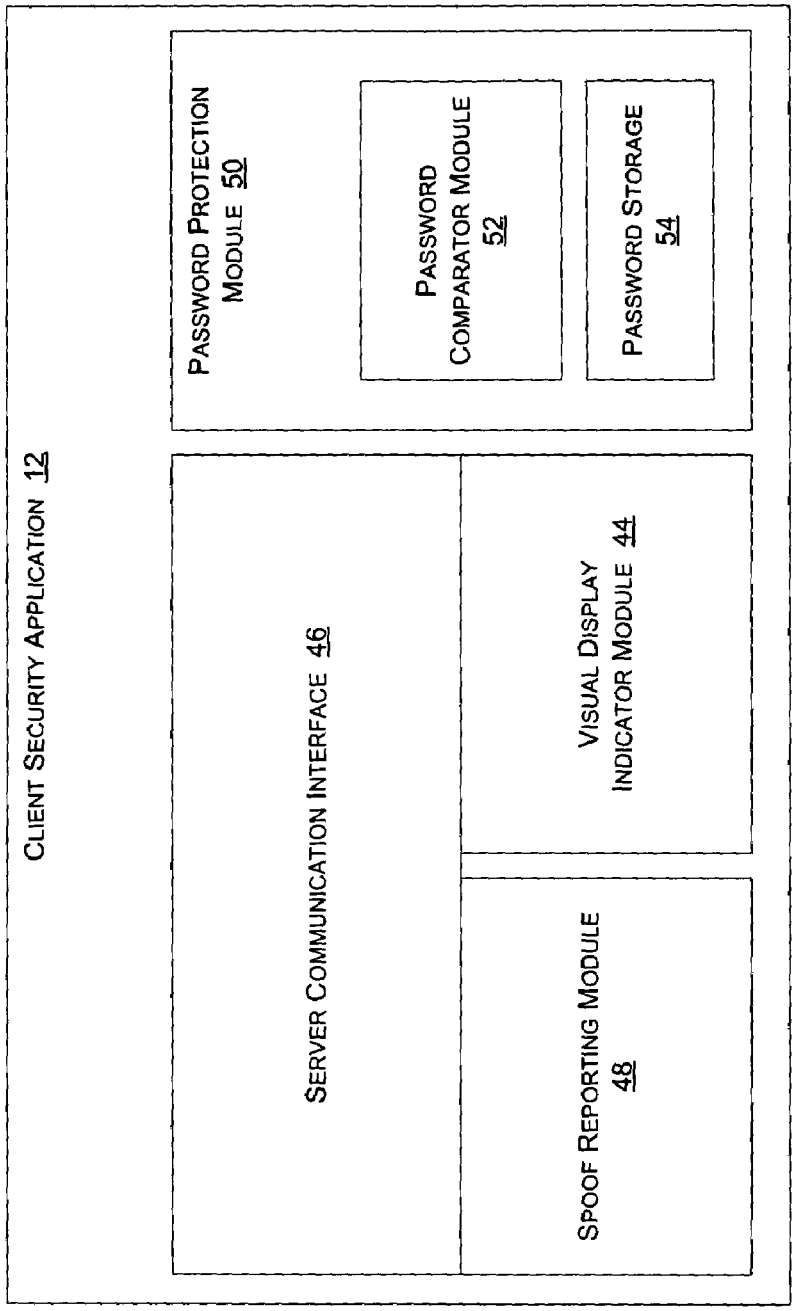
FIG. 5 illustrates a security server application for an embodiment of the present invention.

FIG. 5 illustrates an alternative embodiment of a client security application 12. For one embodiment of the invention, the client security application 12 does not maintain a local black list or a local white list. Instead, after the user has downloaded a document via the client browser application 18, the client security application 12 communicates the URL of the downloaded document to the security server application 14 via the server communication interface 46. The security server application 14 compares the URL of the downloaded document to its master lists and generates a security ranking that is communicated back to the client security application 12. The client security application 12 receives the security ranking via the server communication interface 46, and the visual display indicator module 44 displays a security indicator to indicate the security ranking associated with the URL of the downloaded document.

Figure 6:
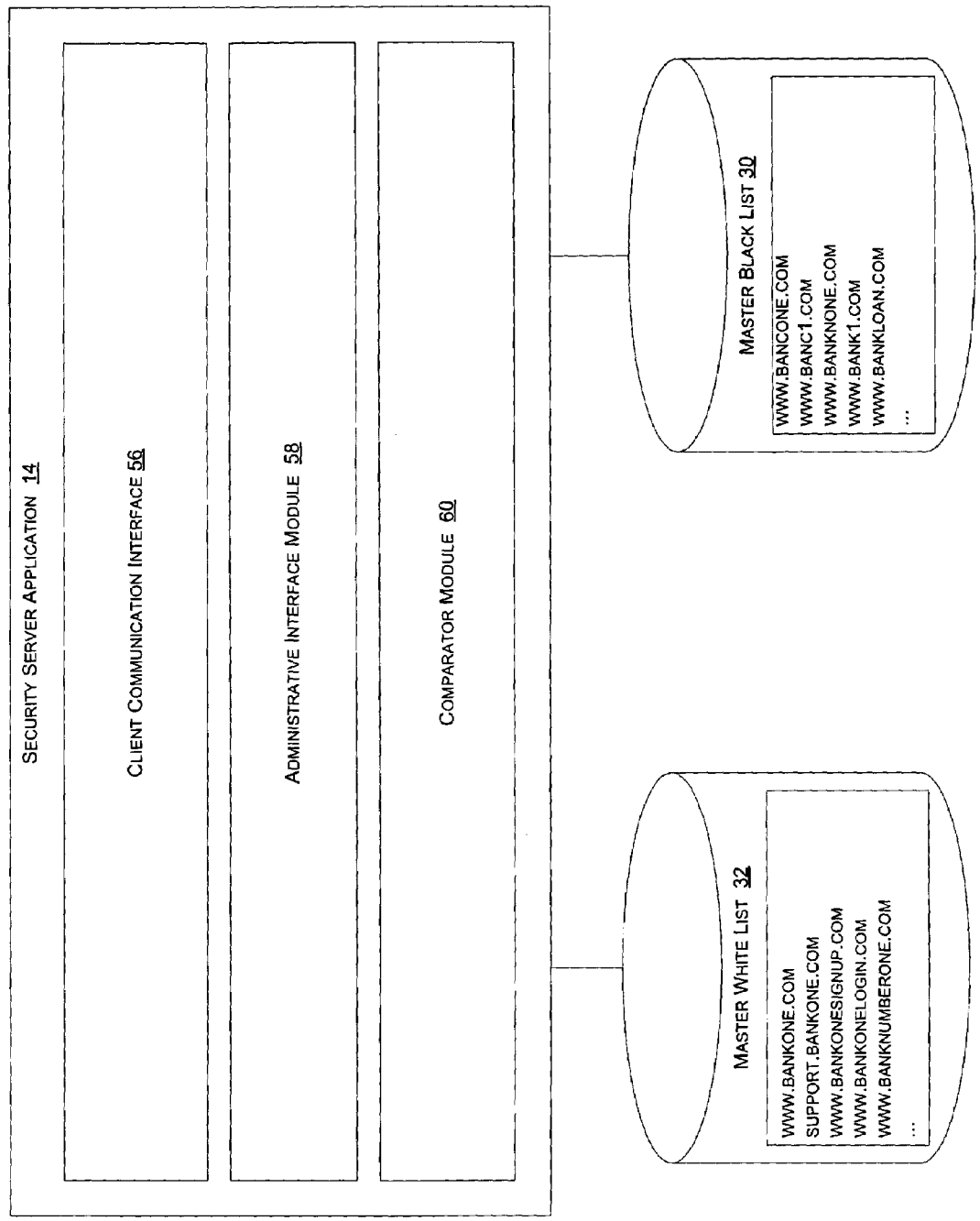
FIG. 6 illustrates a security server application for another embodiment of the present invention.

FIG. 6 illustrates an embodiment of a security server application 14 for use with an embodiment of the client security application 12 described with reference to FIG. 5. The security server application 14 illustrated in FIG. 6 includes a client communication interface 56, an administrative interface module 58, and a comparator module 60. For one embodiment of the invention, the client communication interface 56 receives from the client security application 12 the URL of a document downloaded by a user. The comparator module 60 compares the URL of the downloaded document to URLs in the master black list 30 and/or the master white list 32. Based on the comparison, the security server application 14 communicates a security ranking to the client security application 12 from which the URL was originally received. Accordingly, the client security application 12 can display a security indicator including the security ranking received from the security server application 14. This particular embodiment of the security server application is advantageous because the security server application 14 does not have to automatically update the local lists of each client security application 12 each time a new spoof site or trusted site is added to the master lists 30 and 32. However, this particular embodiment may result in greater network traffic if there are a large number of client security applications 12 requesting security rankings.

Figure 7:
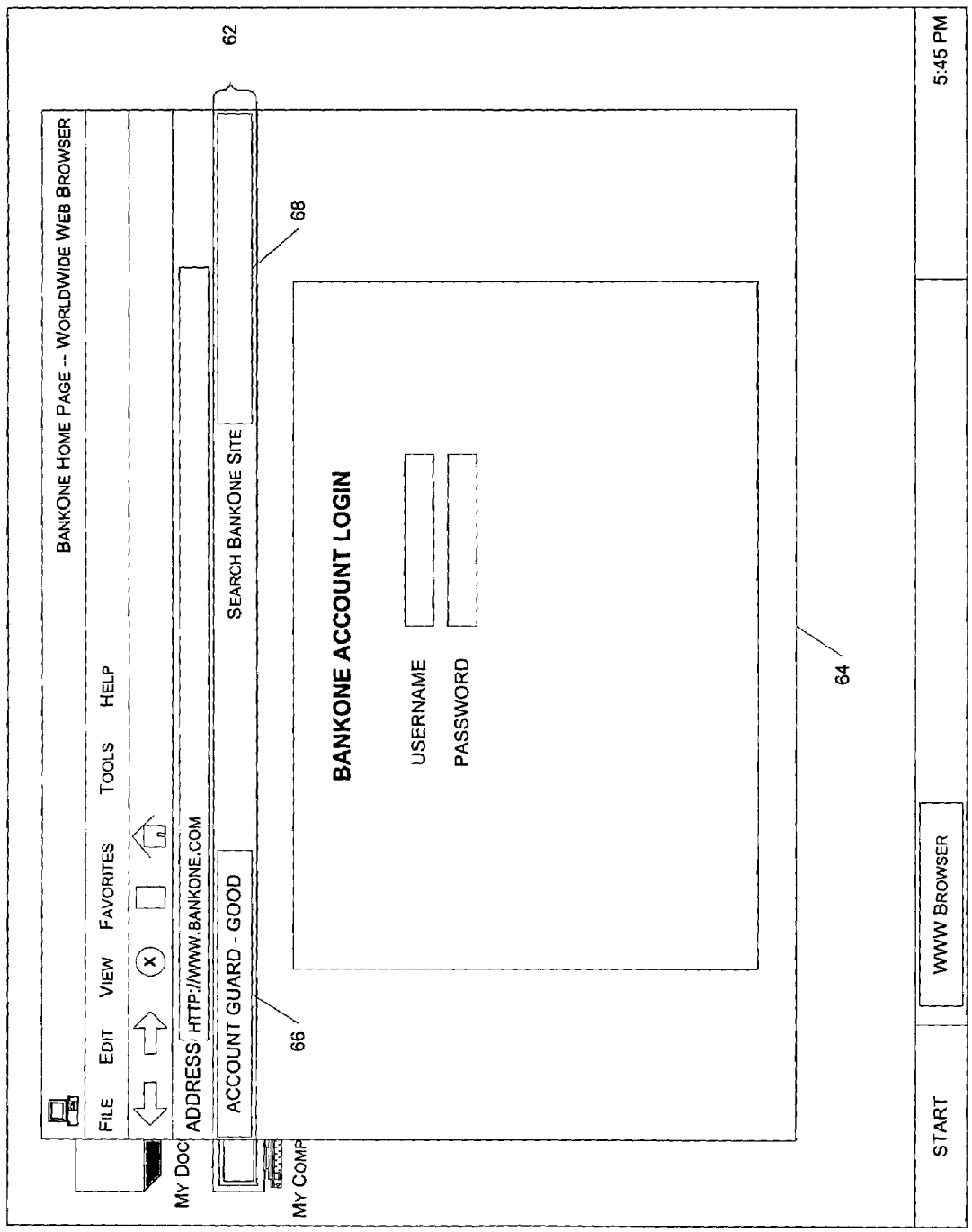
FIGS. 7-12 illustrate various user interfaces consistent with various embodiments of the present invention.

FIGS. 7 through 12 illustrate various user interfaces for various embodiments of the present invention. For example, FIG. 7 illustrates a user interface for an embodiment of a client security application 12 implemented as a toolbar 62 that attaches to a window 64 of a web browser client application 18. The toolbar 62 illustrated in FIG. 7 includes a security indicator 66 to indicate the security ranking of the document that is being viewed in the web browser window 64. For example, as illustrated in FIG. 7, the security indicator 66 indicates that the current URL in the web browser's address bar, www.bankone.com, has a security ranking of "GOOD."

It will be appreciated that any number of security indicator schemes may be used to communicate the security ranking of the downloaded document. For example, instead of simply displaying the word "GOOD" in the security indicator 66 as illustrated in FIG. 7, for other embodiments of the invention, the security indicator scheme may include changing the color of the security indicator 66 according to the security ranking associated with the downloaded document. For example, for one embodiment of the invention, a green colored security indicator 66 indicates that the downloaded document is associated with a known trusted site. Similarly, a downloaded document associated with a known spoof site may cause the security indicator 66 to change to a red color. If the URL of a downloaded document is not in the local black list 38, or the local white list 40, the security indicator 66 may appear as a neutral color, such as grey.

It will be appreciated that other utilities and tools specific to a particular online enterpriser may be included on the toolbar 62 as well. For example, as illustrated in FIG. 7, the toolbar 62 includes a search tool to search the bankone.com web site.

Figure 8:
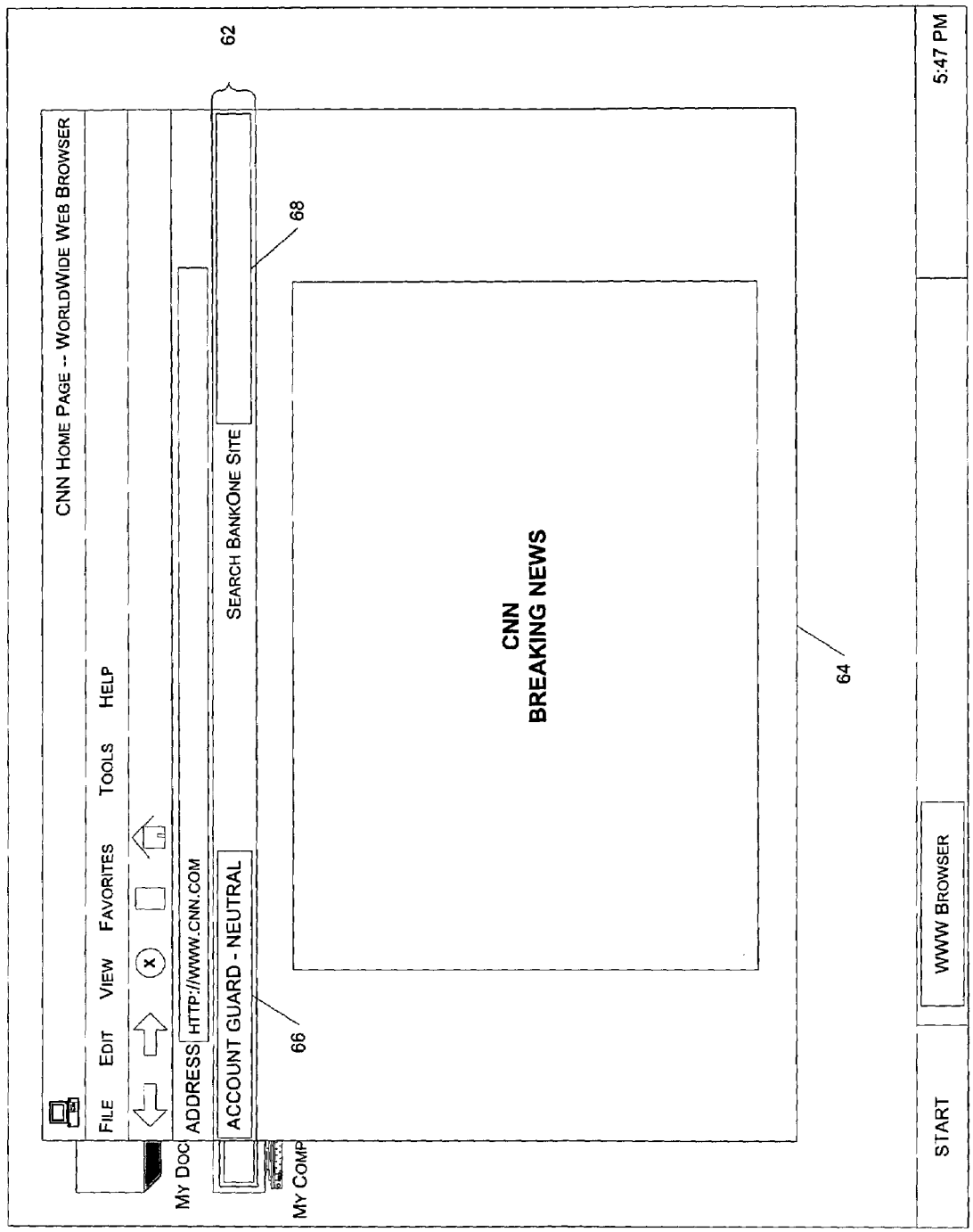

FIG. 8 also illustrates a user interface of an embodiment of a client security application 12 implemented as a toolbar 62 that attaches to a window 64 of a web browser client application 18. The security indicator 66 of the toolbar 62 illustrated in FIG. 8 indicates that the current URL in the web browser's address bar, www.cnn.com has a security ranking of "NEUTRAL." For one embodiment of the present invention, when a particular URL is not found in a black list, or a white list, then the security ranking is considered to be neutral. For one embodiment of the invention, the client security application 12 changes the color of the security indicator 66 to a neutral color, such as grey, to indicate a neutral security ranking.

Figure 9:
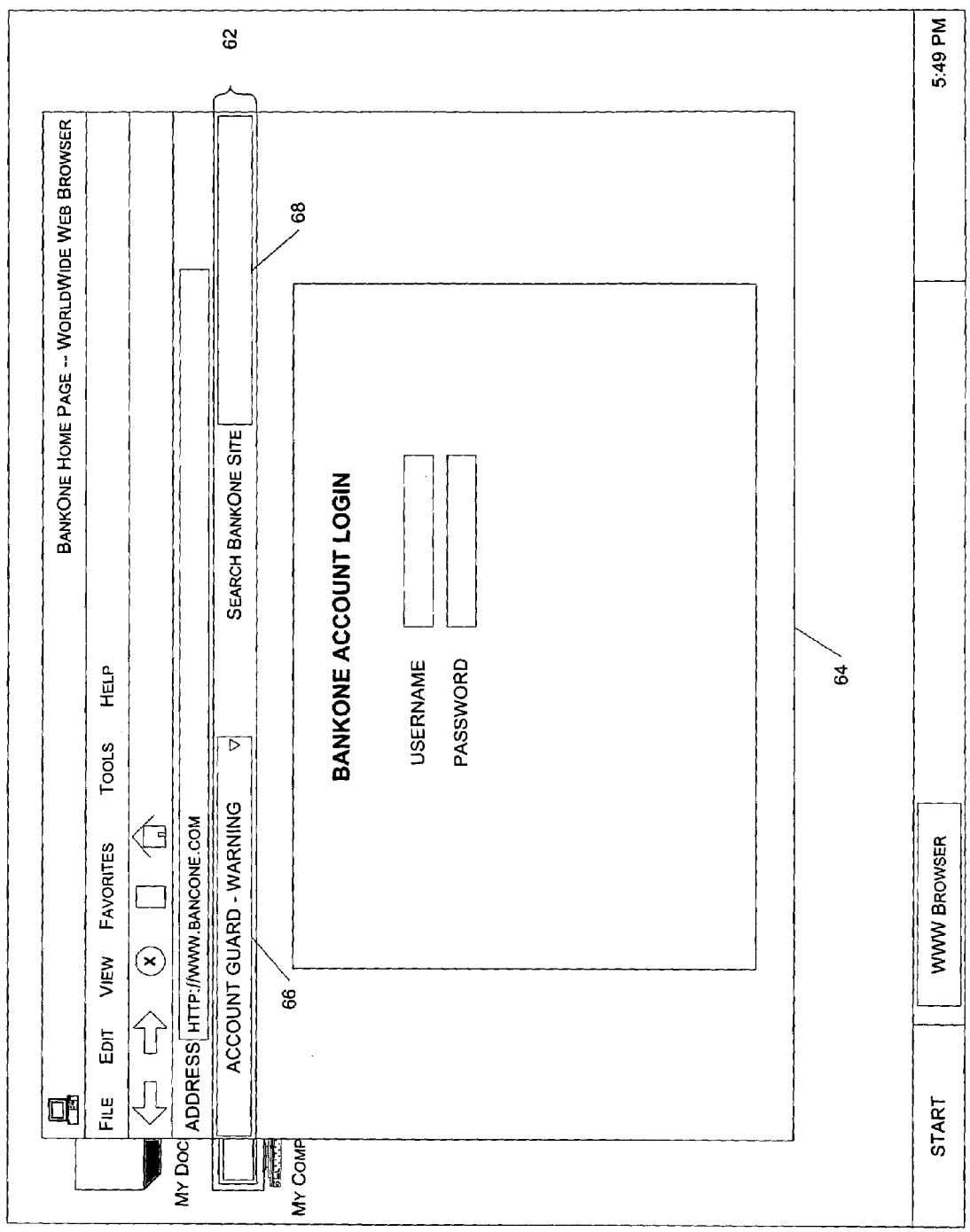

FIG. 9 also illustrates a user interface of an embodiment of a client security application 12 implemented as a toolbar 62 that attaches to a window 64 of a web browser client application 18. The security indicator 66 of the toolbar 62 illustrated in FIG. 9 indicates that the current URL in the web browser's address bar, www.bancone.com, has a security ranking of "WARNING." For purposes of describing the present invention, the URL, www.bancone.com, is a spoof of the site hosted at www.bankone.com. For one embodiment of the present invention, when a particular URL is found in a black list, then the security indicator shows a warning. The client security application 12 may change the color of the security indicator 66 to red, to indicate that the user should be cautious about submitting any personal information to the spoof site, for one embodiment of the invention.

Figure 10:
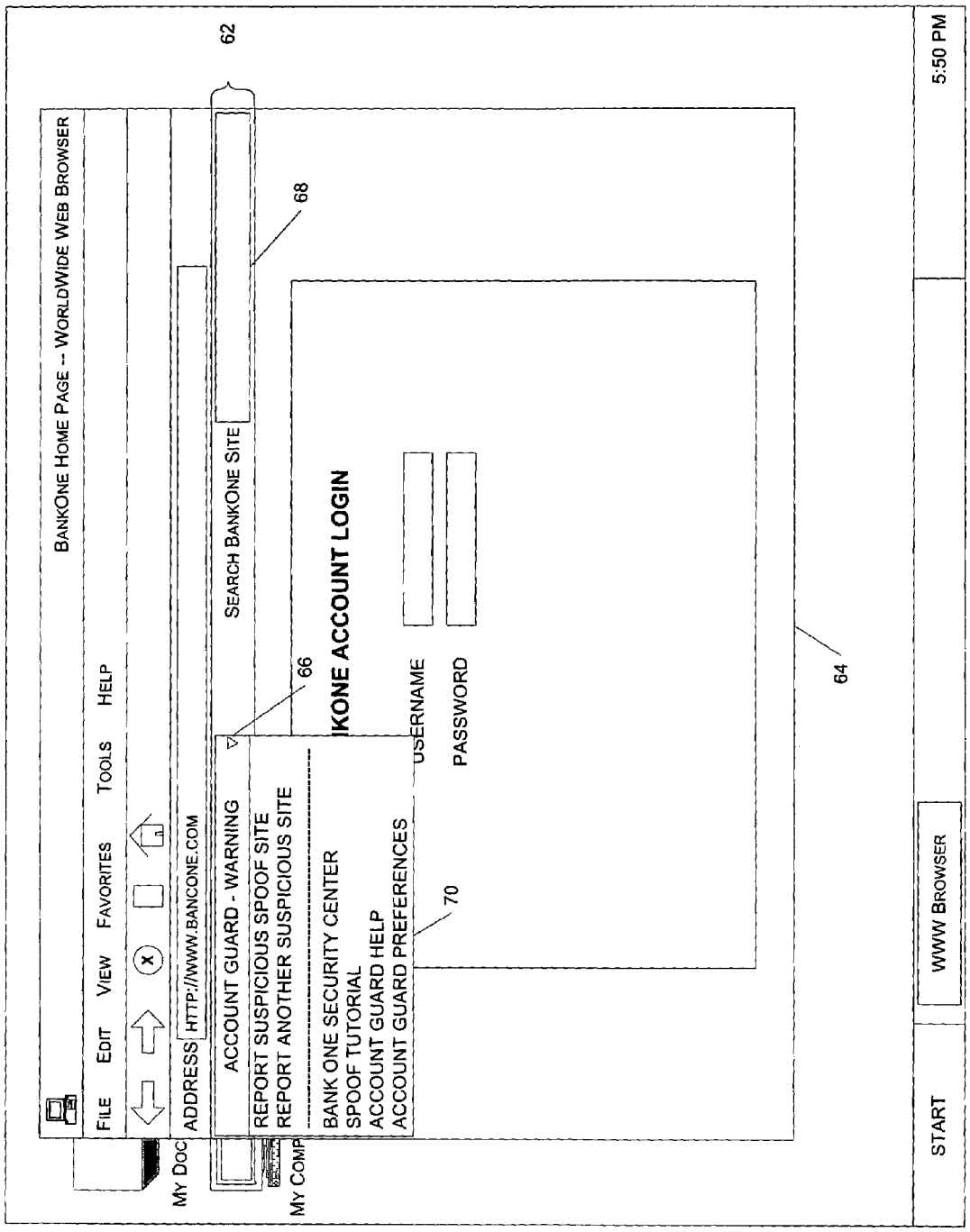

Similar to FIGS. 7 through 9, FIG. 10 also illustrates a user interface for an embodiment of a client security application 12 implemented as a toolbar 62 that attaches to a window 64 of a web browser client application 18. As illustrated in FIG. 10, the security indicator 66 includes a pull down menu 70 for one embodiment of the invention. The pull down menu 70 may have several selectable buttons. For one embodiment of the invention, the pull down menu 70 has a button that allows a user to report a potential spoof site. For example, for one embodiment of the invention, by selecting the "REPORT SUSPICOUS SPOOF SITE" button from the pull down menu 70, the client security application 12 automatically generates an email containing the URL of the most recently downloaded document, www.bancone.com, and allows the user to send the email to an administrator. The spoof reporting module 48 of the client security application 12 may be configured to automatically address the email to an administrator associated with a particular online enterprise, or alternatively, to a third party security service administering a security server application. For one embodiment of the invention, the spoof-reporting module 48 may generate an email that can be edited by the user to include URLs of potential spoof sites other than the URL of the most recently downloaded document.

Figure 11:
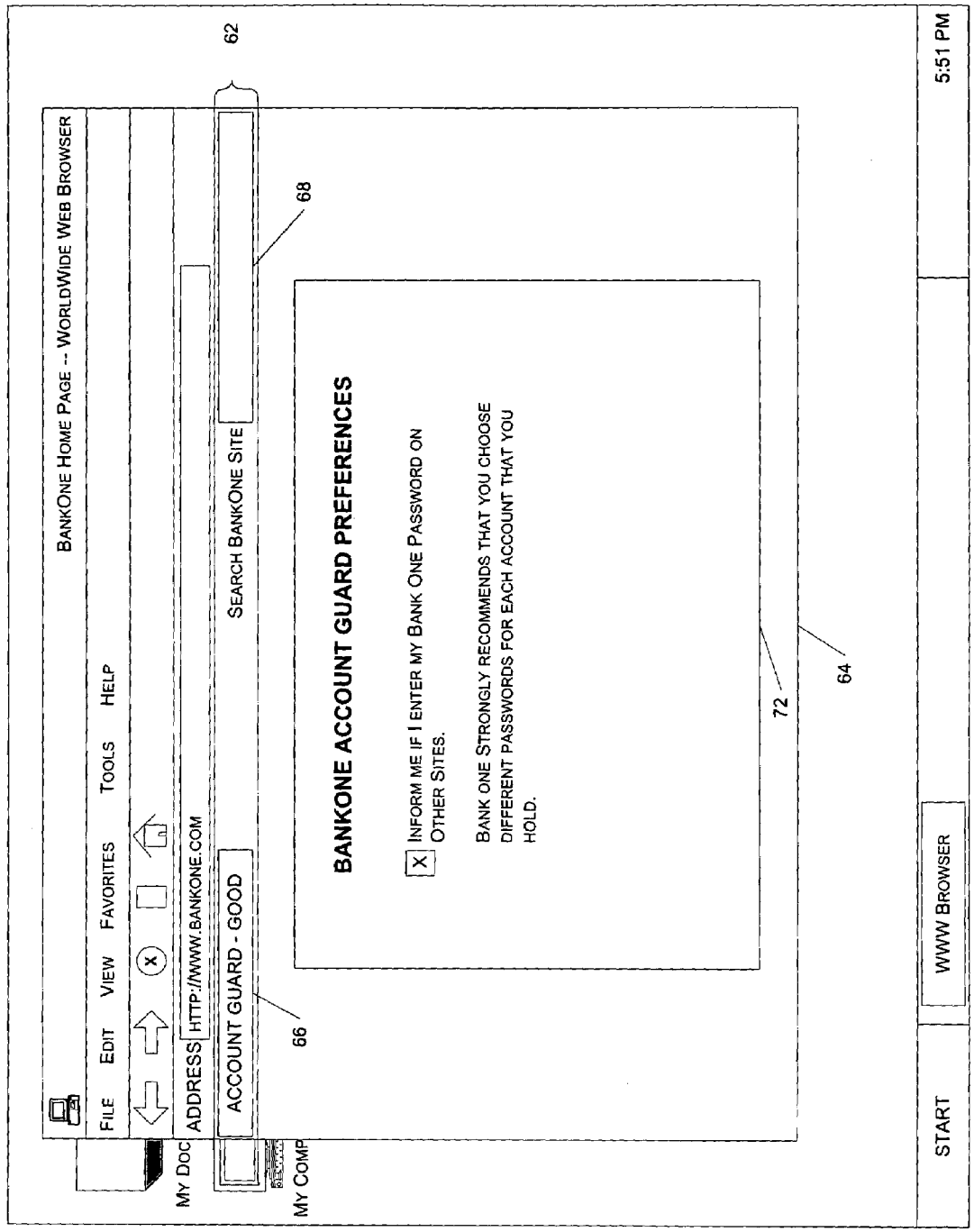

FIG. 11 illustrates a user interface associated with the password protection module 50 of an embodiment of a client security application 12. As illustrated in FIG. 11, the client security application 12 may present the user with a password protection configuration document 72 allowing the user to configure and/or enable password protection. For example, after logging in to a particular account associated with a particular online enterprise, a user may configure the password protection module 50 of the client security application 12 to warn the user if he or she attempts to submit his or her password for that particular account to a server that is not associated with that particular online enterprise and/or account.

Figure 12:
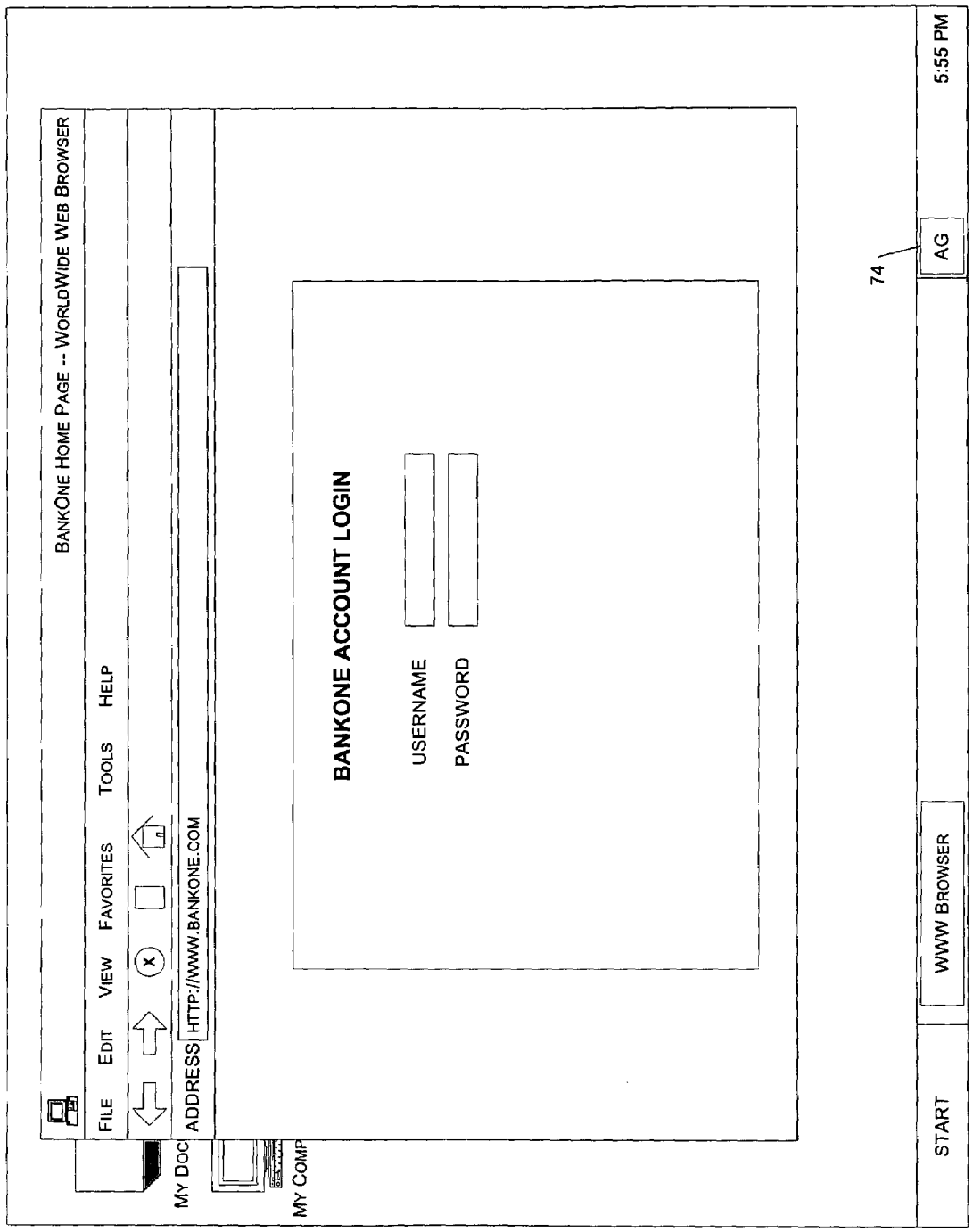

FIG. 12 illustrates a user interface for an embodiment of a client security application 12 implemented as a system tray application for the graphical user interface of a window-based operating system. For one embodiment of the present invention, the client security application 12 is presented to the user as a simple system tray icon 74 that acts as a security indicator. For example, for one embodiment of the present invention, the system tray icon 74 will change colors based on the security ranking of each document downloaded via a client browser application.

Figure 13:
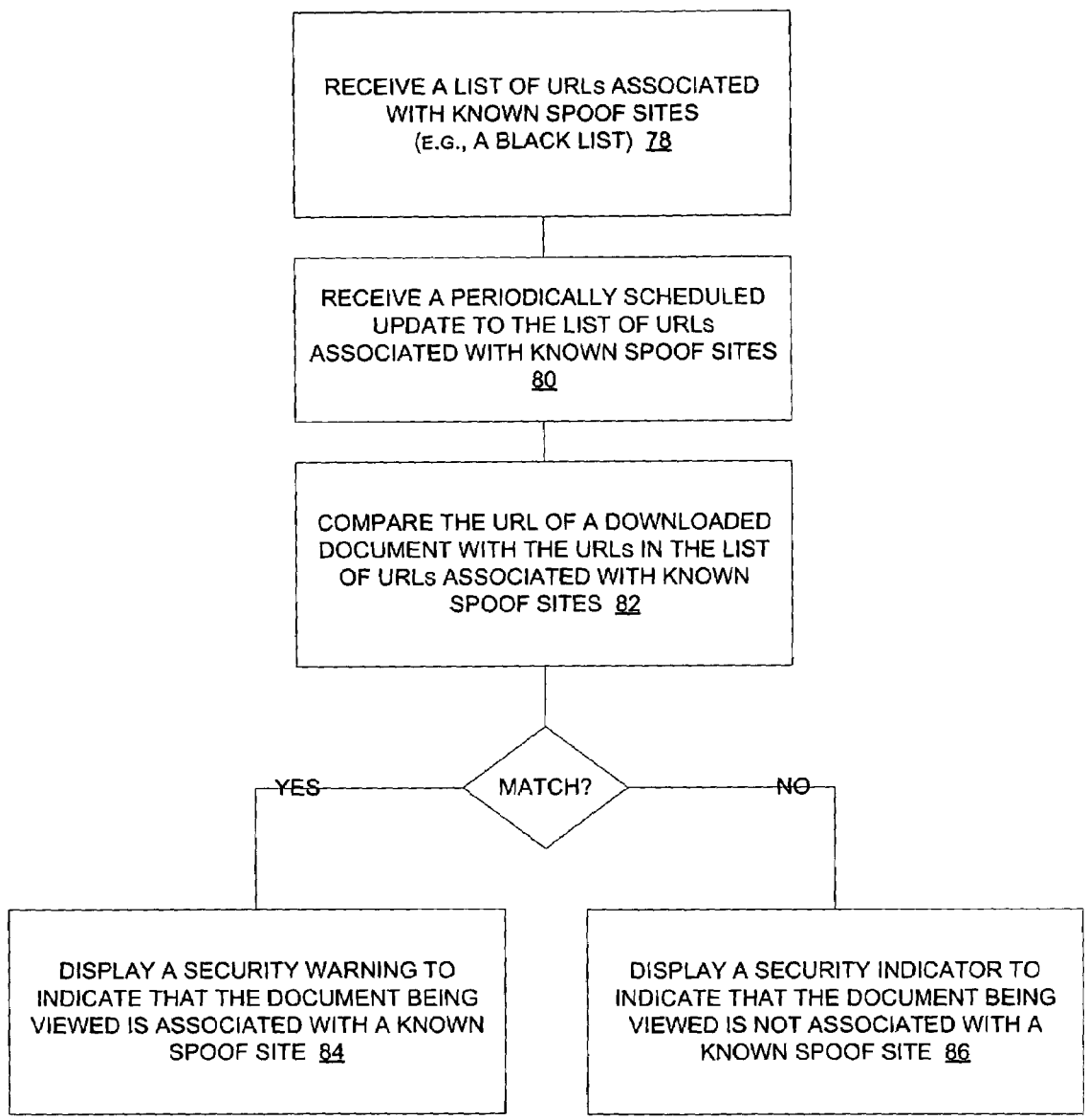
FIGS. 13-16 illustrate flowcharts for various methods for protecting a user against potentially fraudulent activities, consistent with one or more embodiments of the present invention.

FIG. 13 illustrates the operations of a method 76 for one embodiment of the invention to protect users against potentially fraudulent activities associated with spoof web sites. According to the method 76, at operation 78 a list of URLs associated with known spoof sites (e.g., a black list 38) is received. For one embodiment of the invention, the local list 38 is received at the time the client security application 12 is downloaded to a user's system and installed. In an alternative embodiment, the list 38 is received from a security server application 14 at a later time.

At operation 80, a periodically scheduled update to the list of known spoof sites 38 is received. For example, for one embodiment of the invention, periodic updates to a client security application's 12 local black list 38 are communicated from a centralized security server application 14. This ensures that the local list 38 is kept current, and accurately corresponds to the security server's 14 master list 30. For one embodiment of the invention, the client security application 12 periodically requests updates from a security server application 14, thereby "pulling" the master list 30 from the security server application 14. Alternatively, for another embodiment, the security server application 14 is periodically scheduled to "push" the master list 30 updates to one or more client security applications 12.

At operation 82, the URL of a document downloaded by a client application 18, such as a web browser, is compared to the list of URLs known to be associated with spoof sites. If the URL of the downloaded document matches a URL in the list of known spoof sites, then at operation 84, the visual display indicator module 44 of the client security application 12 displays security warning to indicate that the document being viewed is associated with a known spoof site. If the URL of the downloaded document does not match a URL from the black list, at operation 86 the visual display indicator module 44 of the client security application 12 displays a visual indicator to indicate that the recently downloaded document is not in the black list, and therefore is not likely a spoof site.

Figure 14:
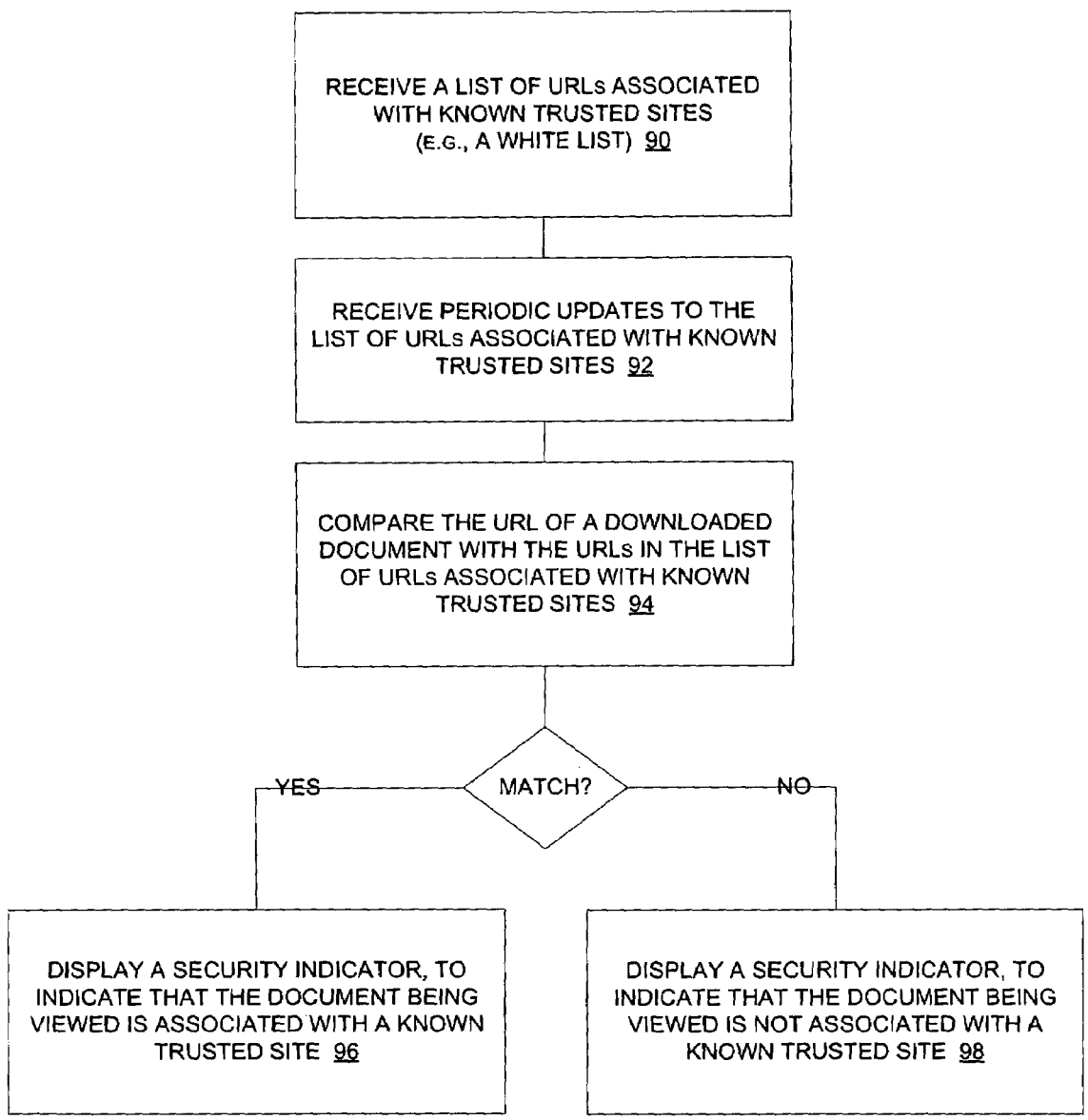

FIG. 14 illustrates the operations of a method 88 for one embodiment of the invention to protect users against potentially fraudulent activities associated with spoof web sites. According to the method 88, at operation 90 a list of URLs associated with known trusted sites (e.g., a white list) is received. For one embodiment of the invention, the list is received at the time the client security application 12 is downloaded to a user's system and installed. In an alternative embodiment, the list is received from a security server application 14 at a later time.

At operation 92, a periodically scheduled update to the list of known trusted sites is received. For example, for one embodiment of the invention, periodic updates to a client security application's 12 local white list 40 are communicated from a centralized security server application 14. This ensures that the local list 40 is kept current.

At operation 94, the URL of a document downloaded by a client application, such as a web browser, is compared to the list of URLs known to be associated with trusted sites 40. If the URL of the downloaded document matches a URL in the list of known trusted sites 40, then at operation 96, the visual display indicator module 44 of the client security application 12 displays a security indicator to indicate that the document being viewed is associated with a known trusted site. If the URL of the downloaded document does not match a URL from the white list 40, at operation 98, the visual display indicator module 44 of the client security application 12 displays a visual indicator to indicate that the recently downloaded document is not associated with a known trusted site. Consequently, the user should use caution when interacting with the site, so as not to unintentionally relinquish confidential and private data, such as a username and/or password.

Figure 15:
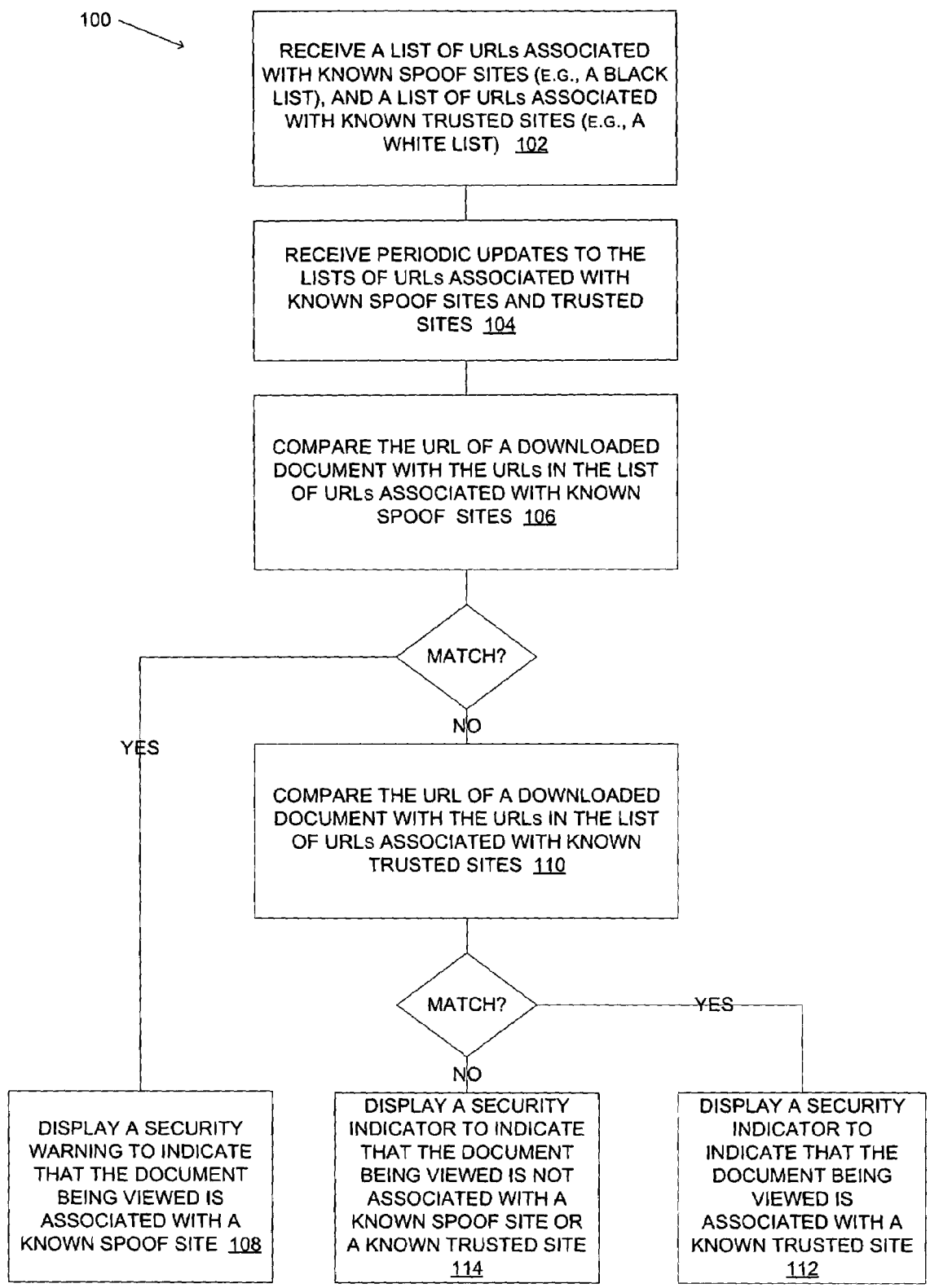

FIG. 15 illustrates the operations of a method 100, for one embodiment of the invention, to protect users against potentially fraudulent activities associated with spoof web sites. According to the method 100, at operation 102 two lists of URLs are received—a list of URLs associated with known spoof sites (e.g., a black list), and a list of URLs associated with known trusted sites (e.g., a white list). At operation 104, a periodically scheduled update to each list is received. At operation 106, the URL of a document downloaded by a client application, such as a web browser, is compared to the list of URLs known to be associated with spoof web sites. If the URL of the downloaded document matches a URL in the list of known spoof web sites, then at operation 108, the visual display indicator module 44 of the client security application 12 displays a security warning to warn the user that the document being viewed is associated with a known spoof site.

However, if the URL of the downloaded document is not in the black list, then, at operation 108, the URL of the downloaded document is compared to the URLs in the list of known trusted sites (e.g., a white list). If the URL of the downloaded document matches a URL from the white list, at operation 112, the visual display indicator module 44 of the client security application 12 displays a visual indicator to indicate that the recently downloaded document is associated with a known trusted site.

However, if the URL of the downloaded document is not in the white list, then at operation 114, the visual display indicator module 44 of the client security application 12 displays a visual indicator to indicate to the user that the URL of the downloaded document is not associated with a known spoof site, or a known trusted site.

Figure 16:
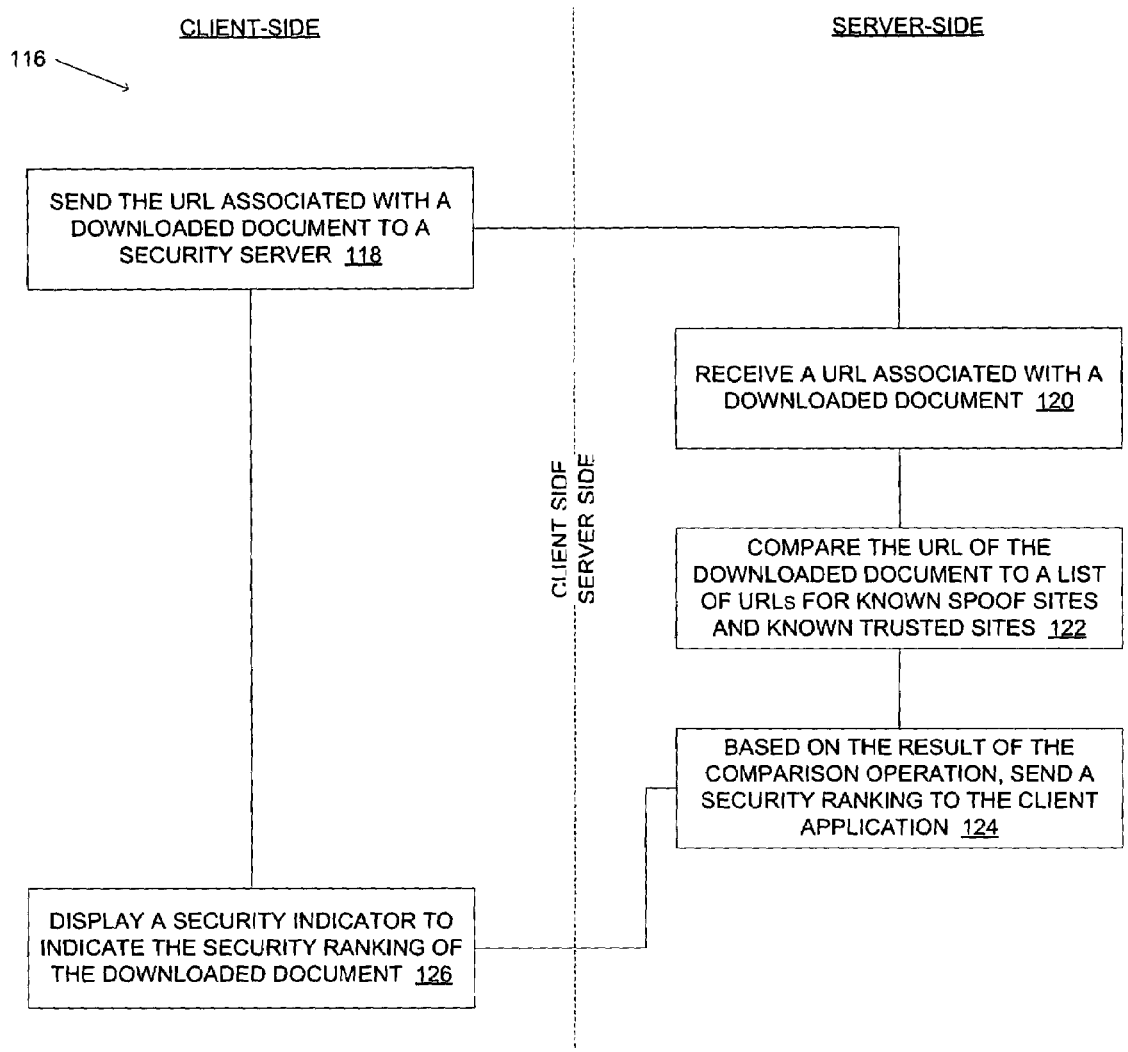

FIG. 16 illustrates the operations of a method 116, for one embodiment of the invention, to protect users against potentially fraudulent activities associated with spoof web sites. The method illustrated in FIG. 16 includes operations that are performed by a server, and operations that are performed by a client. For example, according to the method illustrated in FIG. 16, at operation 118 a client security application 12 sends the URL of a recently downloaded document to a security server 14. At operation 120, the security server application 14 receives the URL sent from the client security application 12. At operation 122, the security server application 14 compares the URL received from the client security application 12 to a list of URLs associated with known spoof sites and a list of URLs associated with known trusted sites. At operation 124, based on the result of the comparisons performed at operation 122, the security server application 14 sends the client security application 12 a security ranking for the downloaded document. At operation 126, the client security application 12 displays a security indicator to indicate the particular security ranking of the downloaded document.

Figure 17:
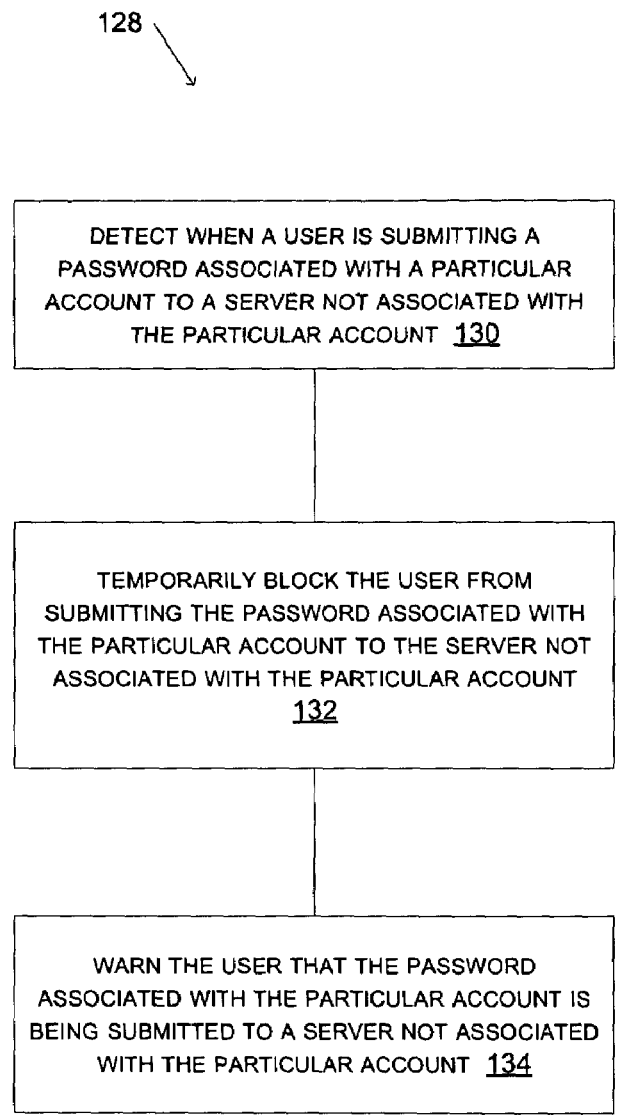
FIG. 17 illustrates the operations for a method to protect a user's password, for one embodiment of the present invention.

FIG. 17 illustrates the operations for a method 128 to protect a user's password, for one embodiment of the present invention. According to the method illustrate in FIG. 17, at operation 130 a password protection module 50 detects when a user is attempting to submit a password associated with a particular account to a server not associated with the particular account. At operation 132, the password protection module 50 temporarily blocks the submission of the password associated with the particular account to the server that is not associated with the particular account. At operation 134, the password protection module 50 warns the user (e.g., by displaying a pop-up window) that he or she is submitting a password associated with a particular account to a server that is not associated with the particular account. For example, a warning may be shown to the user if the user attempts to submit the password associated with the user's bankone.com account to a server hosting a site for a spoof site, such as www.bancone.com, or to another financial site, such as WellsFargo.com.

Figure 18:
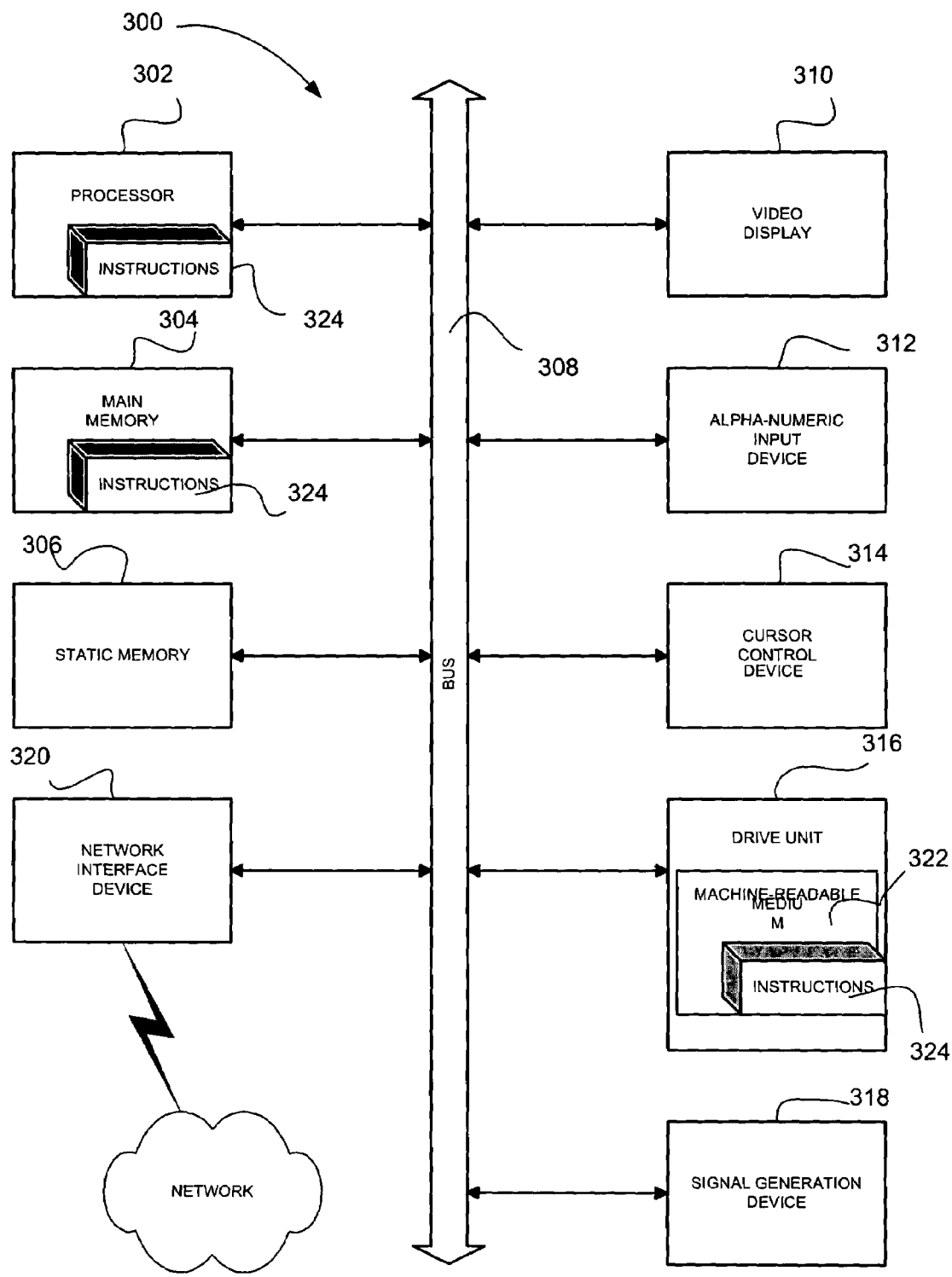
FIG. 18 shows a diagrammatic representation of a machine in the exemplary form of a computer system within which a set of instructions, for causing the machine to perform any one or more of the methodologies discussed herein, may be executed.

FIG. 18 shows a diagrammatic representation of a machine in the exemplary form of a computer system 300 within which a set of instructions, for causing the machine to perform any one or more of the methodologies discussed herein, may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer, or distributed, network environment. The machine may be a server computer, a client computer, a PC, a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Furthermore, while only a single machine is illustrated, the term "machine" shall also be taken to include any collection of machines that individually or jointly execute a set (or multiple sets) of instructions to perform any one or more of the methodologies discussed herein.

The exemplary computer system 300 includes a processor 302 (e.g., a central processing unit (CPU) a graphics processing unit (GPU) or both), a main memory 304 and a static memory 306, which communicate with each other via a bus 308. The computer system 300 may further include a video display unit 310 (e.g., a liquid crystal display (LCD) or a cathode ray tube (CRT)). The computer system 300 also includes an alphanumeric input device 312 (e.g., a keyboard), a cursor control device 314 (e.g., a mouse), a disk drive unit 316, a signal generation device 318 (e.g., a speaker) and a network interface device 320.

The disk drive unit 316 includes a machine-readable medium 322 on which is stored one or more sets of instructions (e.g., software 324) embodying any one or more of the methodologies or functions described herein. The software 324 may also reside, completely or at least partially, within the main memory 304 and/or within the processor 302 during execution thereof by the computer system 300, the main memory 304 and the processor 302 also constituting machine-readable media. The software 324 may further be transmitted or received over a network 326 via the network interface device 320.

While the machine-readable medium 392 is shown in an exemplary embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present invention. The term "machine-readable medium" shall accordingly be taken to include, but not be limited to, solid-state memories, optical and magnetic media, and carrier wave signals.

Thus, a method and system for protecting users against fraudulent activities associated with spoof web sites have been described. Although the present invention has been described with reference to specific exemplary embodiments, it will be evident that various modifications and changes may be made to these embodiments without departing from the broader spirit and scope of the invention. Accordingly, the specification and drawings are to be regarded in an illustrative rather than a restrictive sense.

What is claimed is:

1. A method, performed at a client security application, of protecting a password from being submitted to a spoof site, the method comprising:
   scanning a form to be posted to a first universal resource locator (URL) for the password;
   comparing the password from the form with passwords stored in a password storage module to identify a matched password from among the passwords, the password storage module further storing a second URL associated with the matched password;
   comparing the first URL to which the password is being submitted with the second URL associated with the matched password; and
   if the first URL does not match the second URL, displaying a warning that the password is being submitted to the spoof site.

2. The method of claim 1, further including:
   temporarily blocking the password from being submitted to the first URL associated with the spoof site.

3. The method of claim 1, wherein the second URL is associated with a trusted site.

4. A system including:
   a password storage module to store a password and a first universal resource locator (URL) associated with the password;
   a password detection module to scan a form for the password and to compare a second URL to which the form is being submitted with the first URL associated with the password, the second URL being associated with a server; and
   a display indicator module to display a security warning when the password is being submitted to the server that is not associated with the first URL.

5. The system of claim 4, wherein the password detection module temporarily blocks the password from being submitted to the server.

6. The system of claim 4, wherein the password detection module is to compare the second URL after the scan and the display indicator module is to display the security warning after the compare.

7. A client security system for preventing a password from being submitted to a spoof site, the client security system comprising:
   a processor-implemented password storage module to store a list of universal resource locators and passwords associated with the universal resource locators;
   a processor-implemented password detection module to detect an attempt to submit the password to a server, the server being associated with a universal resource locator;
   a processor-implemented password comparison module to compare the password being submitted with the passwords stored in the password storage module to identify a matched password from among the passwords, and further to compare the universal resource locator associated with the server with a universal resource locator associated with the matched password; and
   a processor-implemented display indicator module to display a security warning based on the comparison of the universal resource locator associated with the server with the universal resource locator associated with the matched password.

8. The client security system of claim 7, wherein the processor-implemented password detection module is to detect the attempt by scanning text fields of a form for the password, the form being posted on the universal resource locator associated with the server.

9. The client security system of claim 8, wherein the text fields are labeled as password fields.

10. The client security system of claim 7, wherein the client security system is to halt the password from being submitted based on a mismatch between the universal resource locator associated with the server and the universal resource locator associated with the matched password.

11. The client security system of claim 7, wherein the universal resource locators stored in the processor-implemented password storage module are associated with trusted sites.

12. The client security system of claim 7, wherein the universal resource locators stored in the processor-implemented password storage module are associated with spoof sites.

* * * * *

UNITED STATES PATENT AND TRADEMARK OFFICE
CERTIFICATE OF CORRECTION

PATENT NO. : 7,606,821 B2  Page 1 of 1
APPLICATION NO. : 10/883454
DATED : October 20, 2009
INVENTOR(S) : Leahy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 817 days.

Signed and Sealed this

Fourteenth Day of December, 2010

David J. Kappos
*Director of the United States Patent and Trademark Office*